United States Patent [19]

Bremer

[11] Patent Number: 4,854,305
[45] Date of Patent: Aug. 8, 1989

[54] RADIOLUCENT TRANSPORT AND DIAGNOSTIC PROCEDURE BOARD

[75] Inventor: Ross L. Bremer, Atlantic Beach, Fla.
[73] Assignee: Bremer Brace of Florida, Inc., Jacksonville, Fla.
[21] Appl. No.: 110,445
[22] Filed: Oct. 20, 1987
[51] Int. Cl.$^4$ ............ A61H 1/02; A61F 5/04; A61F 13/00
[52] U.S. Cl. ............ 128/75; 128/84 C; 128/870
[58] Field of Search ............ 128/69, 70, 71, 75, 128/78, 83, 84 R, 84 C, 85, 133, 134, 870; 5/81, 82

[56] References Cited

U.S. PATENT DOCUMENTS

| | | | |
|---|---|---|---|
| 387,749 | 5/1943 | Linthout | 128/75 |
| 2,191,097 | 2/1940 | Morrison | 128/85 |
| 2,377,940 | 6/1945 | Hughes | 128/75 |
| 2,811,965 | 11/1957 | Richards | 128/75 |
| 3,358,141 | 12/1967 | Hoffmann et al. | 128/134 |
| 3,648,305 | 3/1972 | Ersek | 378/180 |
| 3,732,863 | 5/1973 | Harrington | 128/75 |
| 4,114,611 | 9/1978 | Lyle et al. | 128/75 |
| 4,151,842 | 5/1979 | Miller | 128/87 R |
| 4,166,459 | 9/1979 | Nightingale | 128/75 |
| 4,356,816 | 11/1982 | Granberg | 128/71 |
| 4,369,982 | 1/1983 | Hein et al. | 128/134 |
| 4,466,427 | 8/1984 | Granberg | 128/71 |
| 4,528,981 | 7/1985 | Behar | 128/870 |
| 4,539,979 | 9/1985 | Bremer | 128/75 |
| 4,566,445 | 1/1986 | Jelsma | 128/70 |
| 4,594,999 | 6/1986 | Nesbitt | 128/87 R |
| 4,612,678 | 9/1986 | Fitsch | 128/134 |
| 4,641,637 | 2/1987 | Rosen | 128/75 |

Primary Examiner—Robert A. Hafer
Assistant Examiner—Michael Brown
Attorney, Agent, or Firm—Nixon & Vanderhye

[57] ABSTRACT

A transportation and procedure board for immobilizing a patient with cervical injuries includes a traction indicating device integrally formed with the board for maintaining traction irrespective of the orientation of the board. The board includes handholds along opposite sides, a plurality of straps for immobilizing the patient and releasably connectable to the board, and a common traction applicator and indicator disposed at the foot of the board. The board is completely self-contained and all parts are formed of materials compatible for use with radiolucent machines, such as C.T., M.R.I. and X-ray machines.

16 Claims, 2 Drawing Sheets

RADIOLUCENT TRANSPORT AND DIAGNOSTIC PROCEDURE BOARD

BACKGROUND AND SUMMARY OF THE INVENTION

The present invention relates to a transportation diagnostic procedure board for medical purposes and particularly relates to a transportation and diagnostic procedure board for patients having cervical or spinal injuries. More particularly, the board is compatible for use with radiolucent machines and procedures such that the patient may remain immobilized on the board during transport and while undergoing the diagnostic procedure.

As those familiar with rescue and emergency equipment for use with injured people will readily appreciate, it is oftentimes critical to completely immobilize the injured person, for example, at the scene of an accident, to avoid exacerbating the individual's injury and occasioning further trauma. This is particularly true with respect to cervical or spinal injuries where movement of the individual immediately subsequent to the injury may result in further, and potentially severe, damage, for example, to the nerves governing motor movement.

Equally critical, however, is the need to maintain the patient immobilized until diagnostic tests can be performed and a course of action outlined, for example, surgery, if indicated. A number of current transportable traction boards are not compatible for use with modern-day diagnostic machines and procedures, such as, radiolucent procedures, including computer-aided tomography (C.T.), X-ray and magnetic resonance imaging (M.R.I.). For example, many boards are formed of metal parts which cause problems in using these diagnostic machines, as well as artifact interference. One solution, of course, is to remove the patient from the transport board and dispose the patient on another support compatible for use with the particular diagnostic machine whereby the desired diagnostic procedure may be performed. However, this is wholly contrary to the need to maintain the patient immobilized until the course of treatment can be ascertained. It is therefore highly desirable to immobilize the patient on a traction board as soon after the injury as possible and to maintain the patient immobilized and in traction on the board both during transport and while the diagnostic procedure are being performed.

In accordance with the present invention, there is provided a transportation and diagnostic procedure board for patients having cervical or spinal injuries wherein the patient may be readily and easily immobilized and placed in traction on the board immediately subsequent to the injury and which board and the various parts thereof providing the traction and immobilization are all self-contained on the board and compatible for use with radiolucent machines and diagnostic procedures. To accomplish this, the board of the present invention is formed of an expanded foam plastic core covered with an acrylic resin lamination. Handholds are integrally formed in the board at longitudinally spaced positions along its opposite sides such that the board can be lifted for transport purposes. Additionally, a pair of elongated strips are secured at laterally spaced positions to the upper surface of the board and extend lengthwise thereof for releasable connection with two or more straps which extend transversely to the board. The straps are disposed at selected longitudinal positions along the board and disposed about the patient's torso. The straps and strips have connecting means, preferably Velcro-type fasteners, such that the patient's torso may be strapped to the board in relative immobilized position.

Integral with the board is a traction applying and indicating device which includes a traction bale or halo for connection with the patient's head, a flexible line including a cleat for adjusting the traction and a traction indicator. Preferably, the board is formed with a central opening extending substantially its full length and terminating in an approximate 180° bend at the head end of the board to open in the direction of the patient's head. A flexible radiolucent compatible rope extends through the opening and is attached at its opposite ends to the bale and traction applying and indicator means, respectively. At the bale, the rope is double-backed and cleated to itself once sufficient traction has been applied to the patient, i.e., on the order of 10-15 pounds.

The traction applying and indicating means is formed integrally with the board adjacent its foot end and is disposed between its upper and lower surfaces, i.e., it is confined within the board such that the profile of the board remains smooth and undisturbed. The traction applying and indicating means includes a housing mounting a resilient or deflectable blade, both housing and blade being formed of a plastic radiolucent compatible material. Particularly, an end of the blade is secured against movement relative to the board, while a blade portion extends freely from the secured end into the chamber of a housing disposed in the board. The blade portion and chamber can be viewed through a translucent window formed in and flush with the upper surface of the board. The opposite end of the rope is secured to the free end of the blade such that, once the blade is deflected to apply the traction, the resiliency of the blade maintains the traction force applied to the patient through the rope. That is, the blade itself, after deflection from a null position, maintains the rope under tension and hence maintains the patient in traction. Additionally, the traction force can be measured as the blade end traverses indicia formed on the indicator housing. Thus, the magnitude of the applied traction force can readily be ascertained by the indicator.

In accordance with a preferred embodiment of the present invention, there is provided a carrying board for a patient and which board is compatible for use with radiolucent procedures comprising an elongated, substantially rigid board having a core formed of a plastic foam material and a plastic outer covering. An elongated opening is formed in the board and extends lengthwise thereof. An elongated flexible element extends through the opening. Traction applying and indicating means are carried by the board and are connected to one end of the flexible element. Traction connecting means are provided for connection with the head of the patient lying on the board and connection with the opposite end of the flexible element. Means are carried by the board for strapping a patient to the board. The traction applying and indicating means, the traction connecting means, the flexible element and the board are formed of materials compatible for use with radiolucent machines and diagnostic procedures.

Accordingly, it is a primary object of the present invention to provide a novel and improved transportation and diagnostic procedure board for cervical or spinal injuries and formed of materials compatible for use with radiolucent machines and diagnostic procedures whereby the board may be used both during transport of the patient and when the patient undergoes radiolucent diagnostic procedures.

These and further objects and advantages of the present invention will become more apparent upon reference to the following specification, appended claims and drawings.

BRIEF DESCRIPTION OF THE DRAWING FIGURES

DETAILED DESCRIPTION OF A PREFERRED EMBODIMENT

Reference will now be made in detail to the present preferred embodiment of the invention, an example of which is illustrated in the accompanying drawings.

Figure 1:
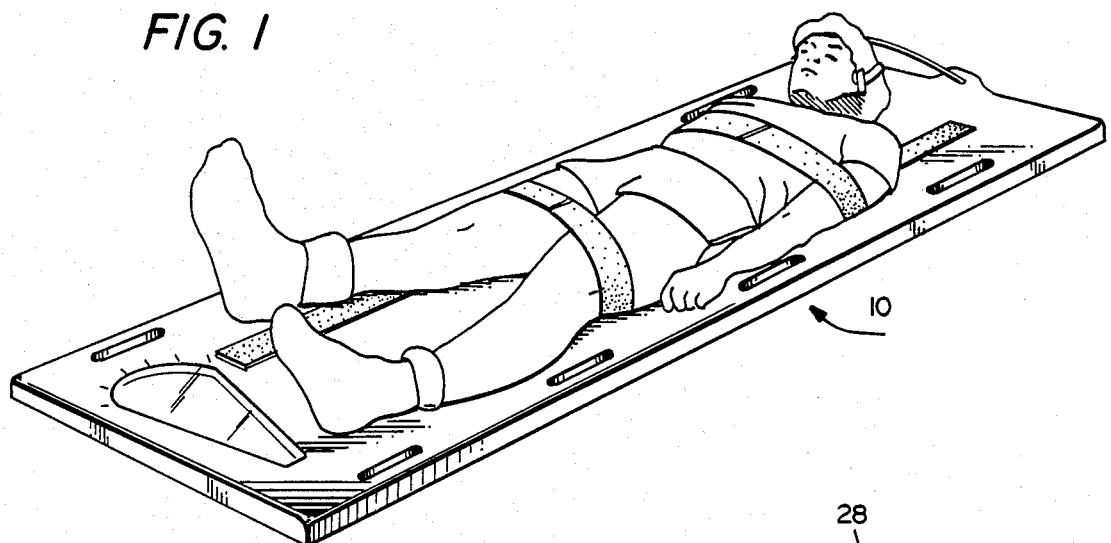
FIG. 1 is a perspective view of a transportation and procedure board constructed in accordance with the present invention and illustrating a patient immobilized and in traction on the board.

Referring now to FIG. 1, there is illustrated a transportation and diagnostic procedure board constructed in accordance with the present invention and generally designated 10. Preferably, the procedure board 10 comprises an elongated, preferably flat, board which has a length and width in excess of the height and width of most individuals whereby the individuals, as indicated in FIG. 1, may lie along the upper surface of the board. Preferably, the board is formed of an expanded inner foam core 12 and an outer shell or cover of an acrylic resin laminate 14. The foam core 12 may comprise a rigid expanded polystyrene foam. Other foams such as polypropylene and polyurethane may also be used. One preferred foam may be a polystyrene foam manufactured under the tradename Airex ™. The outer cover 14 is preferably formed of an acrylic resin reinforced with carbon fiber, Kevlar and woven glass.

Figure 2:
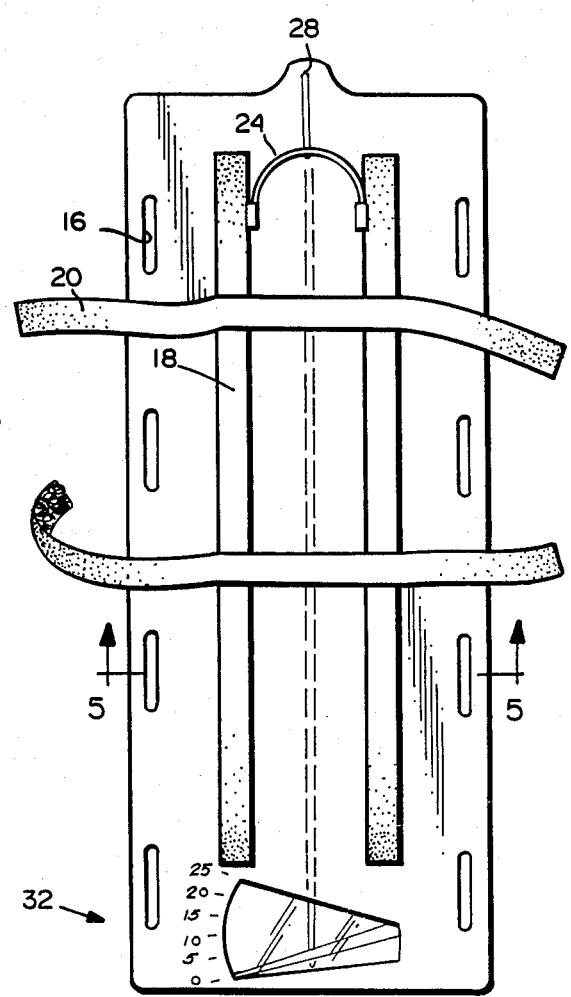
FIG. 2 is a plan view of the board illustrated in FIG. 1.

As best illustrated in FIGS. 1 and 2, a plurality of longitudinally spaced handholds 16 are integrally formed along the lateral margins of board 10 at longitudinally spaced positions therealong, whereby the board with an individual lying thereon may be picked up and transported. The handholds thus constitute elongated slots sufficiently wide to receive the hands of individuals carrying the board.

In order to immobilize a patient lying on board 10, means are provided for strapping the patient to the board. Such means, for example, may include a pair of laterally spaced elongated strips 18 secured along their underside, for example, by adhesive, to the upper surface of board 10. The strips are provided with connecting means which cooperate with connecting means formed on two or more laterally extending straps 20. Preferably, the connecting means constitute the hooks or loops of Velcro-type fasteners. The strips 18 extend longitudinally of the board substantially its full length whereby, depending upon the number of straps 20 used, the patient may be strapped to the board at various positions along the patient's torso and along the board. The straps 20, as indicated above, have cooperating means, preferably the hooks or loops of Velcro-type fasteners, for cooperation with the opposing hooks or loops, respectively, of the Velcro-type fasteners carried by the strips 18 whereby the straps 20 can be longitudinally positioned along board 10 and secured thereto simply by pressing the straps onto the strips 18. Likewise, the straps may extend about the patient's torso and be secured in position to substantially immobilize the patient on the board simply by overlaying the end of one strap over the opposite end of such strap. It will be appreciated that such opposite ends will have hooks and fasteners of the Velcro type which cooperate one with the other.

A central opening 27 is formed longitudinally through the board and opens through an upwardly and rearwardly directed aperture 28 through the upper board surface adjacent the head end of the board. A tubular sleeve 30 extends in the opening 27, the opening 27 and sleeve 30 making an approximately 180° turn at the head end of the board whereby the sleeve and opening open rearwardly in a direction toward the head of the patient. Opening 27 and sleeve 30 at their opposite ends open into a compartment 29 formed at the foot end of the board and which forms part of the traction applying and indicating means hereof which will now be described.

In accordance with the present invention, a traction applying and indicating means 32 is provided and includes a bale or halo 24 adapted for securement to the head of an individual lying on the board. Such bale or halo may be of the type described and illustrated in U.S. Pat. No. 4,539,979 of common assignee herewith. The bale 24 is connected to a flexible element or rope 26, i.e., a rope or line, formed, for example, of Kevlar. Element 26 extends through opening 28 at the head of the board for passage through sleeve 30.

Figure 3:
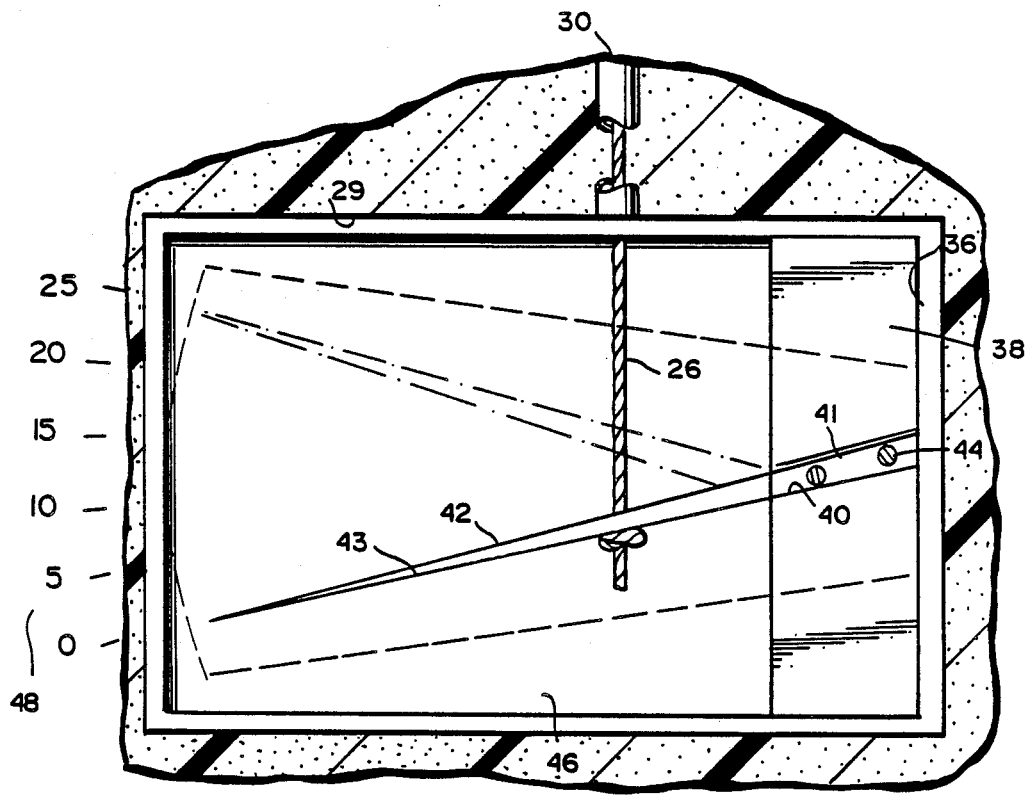
FIG. 3 is an enlarged fragmentary cross-sectional view of one end of the board illustrating the traction indicator.
Figure 4:
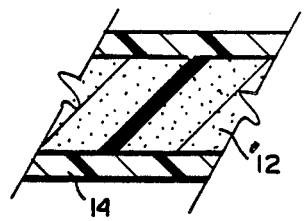
FIG. 4 is an enlarged cross-sectional view taken through the board illustrating its construction.
Figure 5:
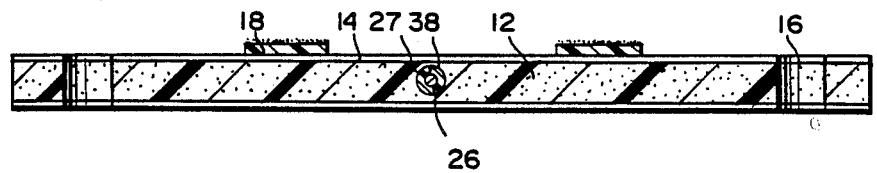
FIG. 5 is a cross-sectional view thereof taken generally about on line 5-5 in FIG. 2.

Traction applying and indicating means 32, as best illustrated in FIG. 3, comprises a housing 36 received in the compartment 29 of the body of board 10. The housing 36 has a mounting block 38 along one side which is grooved or slotted at 40 to receive an end of a resilient or deflectable blade 42. That is, the end 41 of blade 42 is rigidly secured in the groove of mounting block 38, for example, by screws 44. The remaining portion 43 of blade 42 extending from fixed end 41 is free for resilient deflecting movement within housing 36. The end of element 26 is secured to the resilient free portion 43 of blade 42.

When blade portion 43 is deflected from a predetermined neutral or null position and thereby biased for return to the neutral or null position, the return bias of the blade portion 43 furnishes the force for tensioning element 26 and applying the traction to the patient. Housing 36 is disposed in the opening in the body such that the housing including all of the elements contained therein either lie flush with the upper and lower surfaces of the housing or are inset from such surfaces. In this manner, the upper and lower surfaces of the board remain smooth and undisturbed. Housing 36 has a translucent covering 46 which preferably lies flush with the upper surface of the board body. Housing 36 may be provided along its upper surface with indicia 48 for indicating the magnitude of the traction force applied by the blade to the patient lying on the board when blade portion 43 is displaced from its neutral position.

It is a particular feature of the present invention that all of the elements of the transportation and diagnostic procedure board 10 hereof are formed of materials compatible for use with radiolucent diagnostic machines. For example, the materials are compatible for use with computer-aided tomography, X-ray and magnetic resonance imaging machines. As an example of the materials used, the sleeve 30 is formed of Teflon and the flexible element 26 is formed Kevlar. The board itself, of course, is formed of expanded polystyrene foam with an acrylic resin covering along its outer surfaces. The acrylic resin coating may be reinforced with carbon fiber, Kevlar and woven glass. The flexible blade 42 of the traction applying and indicating means is formed of polypropylene and has a clear acrylic transparent cover 46. The straps are preferably formed of a combination of foam and nylon tricot.

In use, straps 20 are adjusted in longitudinal position along the board and relative to one another such that the patient may be strapped to the board in an immobilized position. It will be appreciated that additional straps may be employed at different longitudinal positions along the board as necessary to immobilize the patient. After the patient is placed on the board, the halo or bale 24 is next attached to the head of the patient and traction is applied by manually tensioning rope 26 against the return bias of the resilient blade portion 43 once deflected from its null position. The rope is then cleated to itself in its tensioned condition. The magnitude of the applied traction is readily ascertainable by reading scale or indicia 48. Consequently, the individual immobilized on the board is placed in traction of a predetermined magnitude by a traction applying and indicating means which is wholly integral with the board. Because the board and ancillary equipment carried thereon are formed of materials compatible for use with radiolucent diagnostic machines and procedures, the patient can be disposed in such diagnostic machine without artifact interference, metal problems or other interference from the board per se. In this manner, the patient can remain in traction from the time the patient is placed on the board to the time that a diagnosis has been made and additional procedures, such as surgery, are indicated.

Thus, it will be appreciated that the objects of the present invention have been fully accomplished in that there has been provided a transport and diagnostic procedure board for immobilizing a patient with cervical or spinal injuries, and which procedure board is compatible for use with radiolucent diagnostic machines and procedures.

While the invention has been described in connection with what is presently considered to be the most practical and preferred embodiment, it is to be understood that he invention is not to be limited to the disclosed embodiment, but on the contrary, is intended to cover various modifications and equivalent arrangements included within the spirit and scope of the appended claims.

What is claimed is:

1. A carrying board for a patient and which board is compatible for use with computer-aided tomography, X-ray and magnetic resonance imaging machines and procedures, comprising:
   an elongated substantially rigid board having a core formed of a plastic material;
   means defining an elongated opening in said board extending lengthwise thereof;
   an elongated flexible element extending through said opening means;
   traction applying and indicating means located within said board and connected to one end of said flexible element;
   traction connecting means for connecting with the head of a patient lying on the board and connected to the opposite end of said flexible element; and
   means carried by said board for substantially immobilizing a patient on the board;
   said opening defining means, traction applying and indicating means, said traction connecting means, said element, said immobilizing means and said board being formed of non-ferrous materials compatible for use with computer-aided tomography, X-ray and magnetic resonance imaging machines and procedures.

2. A board according to claim 1 wherein said board has upper and lower surfaces, said traction applying and indicating means lying wholly within the upper and lower surfaces of said board.

3. A board according to claim 2 wherein said traction applying and indicating means includes a traction indicator and a transluscent cover whereby at least a portion of said indicator is exposed to view through said transluscent cover.

4. A board according to claim 1 including handholds carried by said board at spaced longitudinal locations along its opposites sides.

5. A board according to claim 1 wherein said opening defining means include a tubular sleeve carried by said board and extending lengthwise along a central portion of said board.

6. A board according to claim 1 including an aperture through said board adjacent an end thereof, said element extending from said traction indicating means through said elongated opening and said aperture for connection with said traction connecting means.

7. A board according to claim 1 wherein said immobilizing means includes a pair of strips secured to said board at laterally spaced positions therealong and at least one strap for disposition about a patient, each of said strap and said strips carrying cooperating connecting means for releasably connecting said strap and said strips one to the other.

8. A board according to claim 7 wherein said strips are elongated and extend lengthwise of said board, and at least a pair of straps for disposition about a patient, each of said pairs of straps and said elongated strips carrying cooperating connecting means for releasably connecting said straps and said strips one to the other at selected longitudinal positions along said board.

9. A board according to claim 8 wherein said releasable connecting means comprises hooks and loops carried by respective ones of said straps and said strips.

10. A carrying board for a patient and which board is compatible for use with computer-aided tomography, X-ray and magnetic resonance imaging machines and procedures, comprising:
    an elongated substantially rigid board having a core formed of a plastic foam material and an outer covering;
    means defining an elongated opening in said board and extending lengthwise thereof;
    traction indicating means disposed adjacent one end of said board;
    traction connecting means adjacent the opposite end of said and located within said board;

means for connecting said traction indicating means and said traction connecting means one to the other; and means carried by said board for strapping a patient on the board, said strapping means including a pair of elongated strips secured to said board at laterally spaced positions therealong to extend generally lengthwise of said board and at least a pair of straps for disposition about a patient, each of said straps and said strips carrying cooperating connecting means for releasably connecting said straps and said strips one to the other at longitudinally selected and space positions along said board;

said opening defining means, traction indicating means, said traction connecting means, said element, said strapping means and said board being formed of materials compatible with computer-aided tomography, X-ray and magnetic resonance imaging machines and procedures.

11. A board according to claim 10 including handholds carried by said board at longitudinally spaced locations along its opposites sides.

12. A carrying board for a patient and which board is compatible for use with radiolucent machines and procedures, comprising:

an elongated substantially rigid board having a core formed of a plastic material;

means defining an elongated opening in said board extending lengthwise thereof;

an elongated flexible element extending through said opening means;

traction applying and indicating means carried by said board and connected to one end of said flexible element;

traction connecting means for connecting with the head of a patient lying on the board and connected to the opposite end of said flexible element;

means carried by said board for substantially immobilizing a patient on the board;

said traction applying and indicating means, said traction connecting means, said element, and said board being formed of materials compatible for use with radiolucent machines and procedures;

said traction applying and indicating means including an elongated resilient indicator blade;

means for securing one end of said indicator blade against movement relative to said board leaving a portion of said blade free for resilient flexing movement away from a null position;

means for connecting said one end of said element to said blade portion;

said traction applying and indicating means including traction indicia whereby, when said element is placed under tension and said blade portion is deflected from said null position, said blade portion maintains said element under tension and registers with said indicia to indicate the magnitude of the traction applied to the patient by said blade.

13. A board according to claim 12 wherein said board has upper and lower generally parallel surfaces, said traction applying and indicating means lying wholly within the upper and lower surfaces of said board with said blade portion being deflected in a plane generally parallel to the planes defining said upper and lower surfaces, said traction applying and indicating means including a transluscent cover whereby at least part of said blade portion is exposed to view through said transluscent cover.

14. A carrying board for a patient and which board is compatible for use with radiolucent machines and procedures, comprising:

an elongated substantially rigid board having a core formed of a plastic material;

means defining an elongated opening in said board extending lengthwise thereof;

an elongated flexible element extending through said opening means;

traction applying and indicating means carried by said board and connected to one end of said flexible element;

traction connecting means for connecting with the head of a patient lying on the board and connected to the opposite end of said flexible element;

means carried by said board for substantially immobilizing a patient on the board;

said traction applying and indicating means, said traction connecting means, said element, and said board being formed of materials compatible for use with radiolucent machines and procedures;

said immobilizing means including a pair of strips secured to said board at laterally spaced positions therealong and at least one strap for disposition about a patient, each of said strap and said strips carrying cooperating connecting means for releasably connecting said strap and said strips one to the other, said strips being elongated and extending lengthwise of said board;

a pair of straps for disposition about a patient, each of said pairs of straps and said elongated strips carrying cooperating connecting means for releasably connecting said straps and said strips one to the other at selected longitudinal positions along said board, said releasable connecting means comprising hooks and loops carried by respective ones of said straps and said strips;

said traction indicating means including an elongated indicator blade extending generally transversely of said board;

means for securing one end of said indicator blade against translational movement relative to said board leaving a portion of said blade free for movement away from a null position;

means for connecting one end of said element to said blade portion, means for biasing said blade portion for movement toward said null position upon movement thereof away from said null position;

indicia carried by said traction indicating means whereby, when said element is placed under tension and said blade portion is moved away from said null position, said biasing means maintains said element under tension, said blade portion being in registration with said indicia to indicate the magnitude of the traction applied to the patient; said board having upper and lower generally parallel surfaces;

said traction indicating means lying between the upper and lower surfaces of said board with said blade portion being moved in a plane generally parallel to the planes defining said upper and lower surfaces; and said traction indicating means including a translucent cover whereby at least a portion of said indicating means is exposed to view through said translucent cover.

15. A board according to claim 14 including handholds carried by said board at longitudinally spaced locations along its opposites sides.

16. A carrying board for a patient and which board is compatible for use with radiolucent machines and procedures, comprising:

an elongated substantially rigid board having a core formed of a plastic foam material and an outer covering;

means defining an elongated opening in said board and extending lengthwise thereof;

traction indicating means disposed adjacent one end of said board;

traction connecting means adjacent the opposite end of said board for connecting with the end of a patient lying on the board;

means for connecting said tractor indicating means and said traction connecting means one to the other;

means carried by said board for strapping a patient on the board, said strapping means including a pair of elongated strips secured to said board at laterally spaced positions therealong to extend generally lengthwise of said board and at least a pair of straps for disposition about a patient, each of said straps and said strips carrying cooperating connecting means for releasably connecting said straps and said strips one to the other at longitudinally selected and spaced positions along said board;

said traction indicating means, said traction connecting means, said element and said board being formed of materials compatible with radiolucent machines and procedures; and said board having upper and lower surfaces lying in generally spaced parallel planes relative to one another, said indicating means lying wholly within the plane of the board between said surfaces.

* * * * *